(12) United States Patent
Clifford et al.

(10) Patent No.: US 12,183,025 B2
(45) Date of Patent: Dec. 31, 2024

(54) SOIL SENSING TARGET SELECTION

(71) Applicant: Deere & Company, Moline, IL (US)

(72) Inventors: David Clifford, San Francisco, CA (US); Emi E. Muranaka, Honolulu, HI (US)

(73) Assignee: DEERE & CO., Moline, IL (US)

( * ) Notice: Subject to any disclaimer, the term of this patent is extended or adjusted under 35 U.S.C. 154(b) by 248 days.

(21) Appl. No.: 17/590,438

(22) Filed: Feb. 1, 2022

(65) Prior Publication Data

US 2023/0245335 A1 Aug. 3, 2023

(51) Int. Cl.
 G06T 7/70 (2017.01)
 B25J 5/00 (2006.01)
 G06V 20/10 (2022.01)
 G06V 20/56 (2022.01)

(52) U.S. Cl.
 CPC ............ *G06T 7/70* (2017.01); *B25J 5/00* (2013.01); *G06V 20/188* (2022.01); *G06V 20/56* (2022.01); *G06T 2207/30188* (2013.01); *G06T 2207/30252* (2013.01)

(58) Field of Classification Search
 CPC . B25J 5/00; B25J 5/007; B25J 19/023; G01N 33/24; G01N 2033/245; G06T 7/70; G06T 2207/30188; G06T 2207/30252; G06V 20/188; G06V 20/56
 See application file for complete search history.

(56) References Cited

U.S. PATENT DOCUMENTS

| | | | |
|---|---|---|---|
| 2018/0168094 A1* | 6/2018 | Koch | G01J 5/07 |
| 2019/0150357 A1* | 5/2019 | Wu | H04N 7/188 |
| 2020/0264154 A1* | 8/2020 | Saez | G01N 33/0098 |
| 2021/0000006 A1* | 1/2021 | Ellaboudy | A01B 69/008 |
| 2021/0158041 A1* | 5/2021 | Chowdhary | G05D 1/0278 |
| 2021/0397836 A1* | 12/2021 | Li | G06N 3/045 |
| 2022/0028048 A1* | 1/2022 | Frei | G06T 7/13 |
| 2022/0117217 A1* | 4/2022 | Wurden | A01B 76/00 |
| 2022/0217894 A1* | 7/2022 | Guo | G06V 20/188 |
| 2022/0262112 A1* | 8/2022 | Young | G06V 20/10 |
| 2022/0318552 A1* | 10/2022 | Chowdhary | G06V 20/56 |

(Continued)

OTHER PUBLICATIONS

An Approach to the Use of Depth Cameras for Weed Volume Estimation—2016 (Year: 2016).*

(Continued)

*Primary Examiner* — Nizar N Sivji
(74) *Attorney, Agent, or Firm* — Fenwick & West LLP

(57) ABSTRACT

Implementations are described herein for optimizing soil sensing spatial selection. In various implementations, object recognition processing may be performed on one or more images captured by a vision sensor carried by a vehicle as the vehicle travels through the agricultural field. Based on the object recognition processing, one or more plants depicted in the one or more images may be identified, and one or more locations of the one or more identified plants relative to the vehicle may be determined. One or more soil sensing targets may be selected on the ground at one or more selected distances from the one or more locations of the one or more identified plants relative to the vehicle. One or more manipulators carried by the vehicle may be operated to perform soil sensing at the one or more soil sensing targets.

20 Claims, 5 Drawing Sheets

(56) References Cited

U.S. PATENT DOCUMENTS

2023/0017425 A1* 1/2023 Bereciartua-Perez ...................... G06T 7/0002

OTHER PUBLICATIONS

A Portable Agricultural Robot for Continuous Apparent Soil Electrical Conductivity Measurements to Improve Irrigation Practices—2021 (Year: 2021).*
A review on the Imaging Approaches in Agriculture with Crop and Soil Sensing Methodologies—2021 (Year: 2021).*
Rossel et al., "Proximal Soil Sensing" Springer. ISBN 978-90-481-8859-1. DOI 10.1107/978-90-481-8859-8. 2010. 440 pages.
Dursun et al., "Optimization of soil moisture sensor placement for a PV-powered drip irrigation system usning a genetic algorithm and artifical neural network" CrossMark. Electr Eng (2017) 99:407-419. DOI 10.1007/s00202-016-0436-8. 13 pages.
Moshou, Dimitrios "vol. 1 Sensors in Agriculture" MDPI. ISBN 978-3-03897-412-3. 2019. 348 pages.
Rix et al., "Irrometer Watermark Series: Location Selection" Mississippi State University. Publication 3539 (11-20). 2020. 2 pages.
Talaviya, et al., "Implementation of artificial intelligence in agriculture for optimisation of irrigation and application of pesticides and herbicides" Artificial Intelligence in Agriculture 4 (2020). pp. 58-73.
Leib et al., "Placement and Interpretation of Soil Moisture Sensors for Irrigated Cotton Production in Humid Regions" Dec. 2015. 8 pages.

* cited by examiner

SOIL SENSING TARGET SELECTION

BACKGROUND

Numerous properties of soil influence crop growth in various ways. These soil properties include, but are not limited to, moisture, pH, organic matter, carbon content, nitrogen content, calcium content, magnesium content, compaction, soil-air permeability, and so forth. Soil analysis is a process by which these soil properties are measured by analyzing soil samples. Lab-based or ex situ soil analysis involves extracting soil samples in the field and analyzing those collected samples elsewhere, e.g., in a laboratory. Field-based or in situ soil analysis, also referred to as "field-based soil sensing" or "proximal soil sensing," involves using active or passive "proximal soil sensors" to analyze the soil in the field, rather than in a lab. As used herein, "soil sensing" will refer to collecting a soil sample at a particular location and analyzing it elsewhere (lab-based soil analysis) or sampling in the field (proximal soil sensing).

SUMMARY

The effectiveness of soil analysis for predicting and/or managing crop growth may depend largely on the locations and/or density at which soil sensing is performed. If samples are taken and/or sensors are placed at suboptimal locations, the information gained may have limited value. Accordingly, implementations are described herein for soil sensing target selection. More particularly, but not exclusively, implementations are described herein for analyzing images captured in the field by a vision sensor carried by a vehicle, identifying locations of plants and/or other objects based on that analysis, and using the locations of the plants and/or other objects, selecting soil sensing targets on the ground proximate the vehicle, e.g., so that the vehicle can perform soil sensing at those selected locations in real time as the vehicle travels through the field.

In some implementations, a method may be implemented by one or more processors while a vehicle travels through an agricultural field, and the method may include: performing object recognition processing on one or more images captured by a vision sensor carried by the vehicle as the vehicle travels through the agricultural field; based on the object recognition processing, identifying one or more plants depicted in the one or more images; determining one or more locations of the one or more identified plants relative to the vehicle; selecting one or more soil sensing targets on the ground at one or more selected distances from the one or more locations of the one or more identified plants relative to the vehicle; and operating one or more manipulators carried by the vehicle to perform soil sensing at the one or more soil sensing targets.

In various implementations, the one or more locations of the one or more identified plants relative to the vehicle may be determined based at least in part on extrinsic parameters of the vision sensor relative to the vehicle. In various implementations, the one or more locations of the one or more identified plants relative to the vehicle may be determined based at least in part on depth measurements obtained by the vision sensor or by another sensor carried by the vehicle.

In various implementations, the selecting may be further based on one or more soil sensing constraints. In various implementations, the one or more soil sensing constraints include an optimal range of distances between a soil sensing target and one or more of the identified plants. In various implementations, the one or more soil sensing constraints include a location on the ground of a prior fertilizer injection. In various implementations, the one or more soil sensing constraints include a location between rows of plants.

In various implementations, the selecting may include optimizing an objective function with respect to the one or more soil sensing targets, subject to the one or more soil sensing constraints. In various implementations, the optimizing may include simulated annealing or linear programming.

In various implementations, one or more of the manipulators may take the form of a robot arm. In various implementations, the robot arm may include an end effector configured to extract a soil sample for subsequent lab analysis. In various implementations, the robot arm may include, as an end effector, a proximal soil sensor.

In addition, some implementations include one or more processors (e.g., central processing unit(s) (CPU(s)), graphics processing unit(s) (GPU(s), and/or tensor processing unit(s) (TPU(s)) of one or more computing devices, where the one or more processors are operable to execute instructions stored in associated memory, and where the instructions are configured to cause performance of any of the aforementioned methods. Some implementations also include one or more non-transitory computer readable storage media storing computer instructions executable by one or more processors to perform any of the aforementioned methods.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

DETAILED DESCRIPTION

Figure 1A:
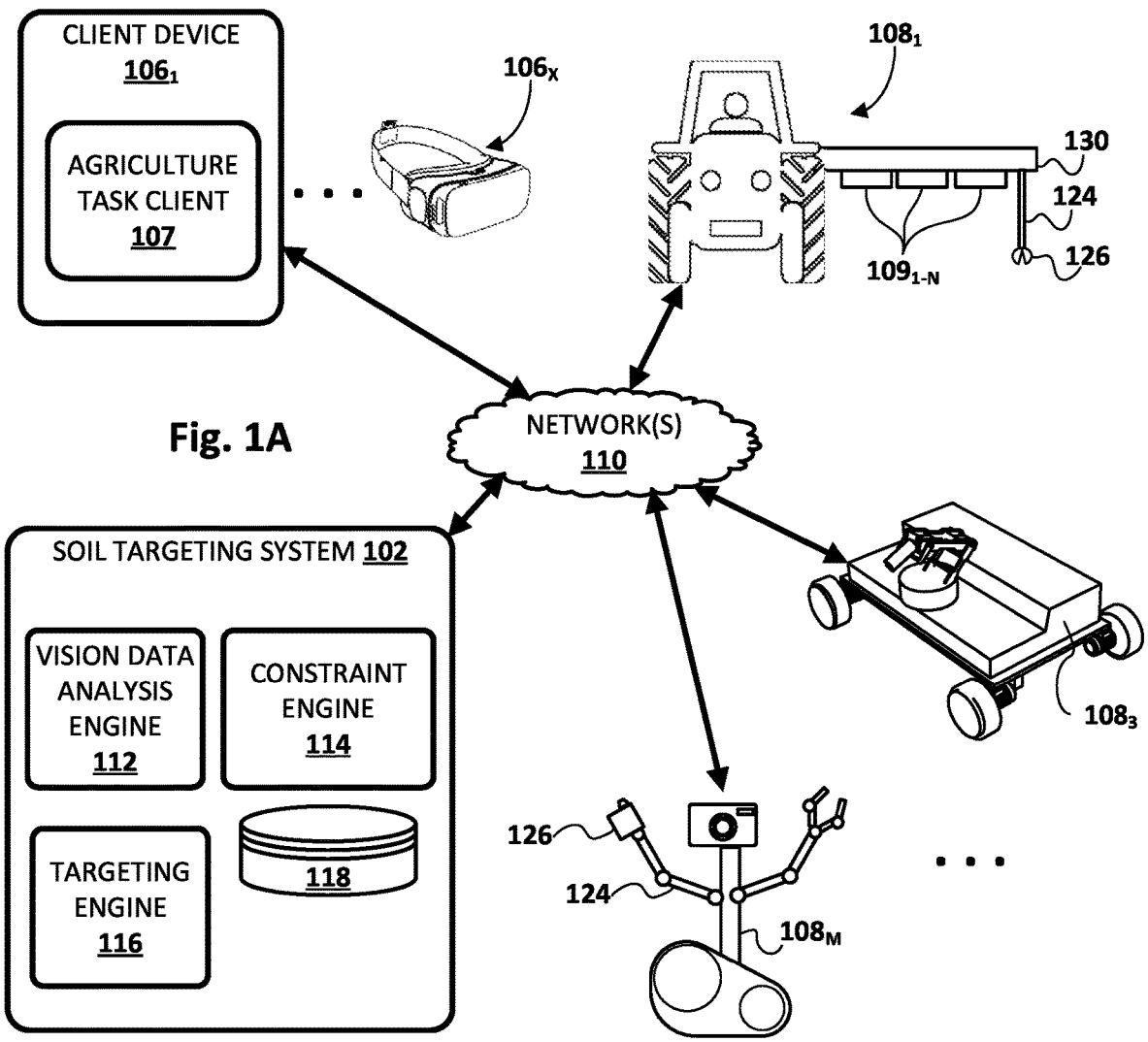
FIG. 1A schematically depicts an example environment in which disclosed techniques may be employed in accordance with various implementations.

The effectiveness of soil analysis for predicting and/or managing crop growth may depend largely on the locations and/or density at which soil sensing is performed. If samples are taken and/or sensors are placed at suboptimal locations, the information gained may have limited value. Accordingly, implementations are described herein for soil sensing target selection. More particularly, but not exclusively, implementations are described herein for analyzing images captured in the field by a vision sensor carried by a vehicle, identifying locations of plants and/or other objects based on that analysis, and using the locations of the plants and/or other objects, selecting soil sensing targets on the ground proximate the vehicle, e.g., so that the vehicle can perform soil sensing at those selected locations in real time as the vehicle travels through the field.

In various implementations, one or more vision sensors may be carried through a field, orchard, plot, etc., by a vehicle such as a tractor (e.g., mounted to the tractor itself or to another mechanism moved by the tractor, such as a spray boom), a center pivot, an agricultural robot, and so forth. In various implementations, such a vehicle may be controlled by a person driving it, remotely, or may have various degrees of autonomy. The vision sensor(s) may be operated to acquire images of the field, such as overhead and/or side views of crops, other plants such as weeds, or other objects.

The images acquired by the vision sensor(s) may be processed, e.g., in real time using logic onboard the vehicle. Various types of object recognition processing may be performed to detect and/or identify plant(s) near the vehicle, such as to one side of the vehicle, underneath the vehicle, in front of or behind the vehicle, etc., and/or to detect other phenomena, such as presence of plant disease, pest infestation, evidence of fire damage, etc. In some implementations, one or more machine learning models, such as a convolutional neural network (CNN), may be trained to detect various types of plants, such as crops being grown deliberately, weeds, or other objects such as sprinkler heads, indicia provided with mulch, pests, plant disease, and so forth. Based on the machine learning model(s), in some implementations, these images may be annotated and/or segmented, e.g., with bounding shapes and/or pixel-wise annotations, to segment and/or annotate plants in those images.

Once plants are segmented and/or annotated in the images, locations of those plants may be determined relative to the vehicle. These physical plant locations relative to the vehicle may be determined based at least in part on extrinsics and/or intrinsics of the vision sensor(s) that captured the images, as well as based on aspects of the acquired images, such as depth measurements (which may also be acquired by other types of sensors). As used herein, "extrinsic parameters" of the vision sensor refers to parameters related to a location and/or orientation of a vision sensor, e.g., relative to some reference point. Put another way, vision sensor extrinsics may refer to a translational location and/or orientation of the vision sensor relative to a world frame, and may be dictated by things such as the vision sensor's rotation, tilt or angle, position on the vehicle, pose of a robot arm or other appendage to which the vision sensor is mounted, and so forth. Vision sensor intrinsic parameters, by contrast, may include optical, geometric and/or digital settings of the vision sensor, such a focal length, zoom, camera lens distortion, etc.

The location(s) of the identified plant(s) relative to the vehicle, as well as those plant(s)' traits detected in the images, may form a current context or state, e.g., of the vehicle. Based on this context or state, one or more soil sensing targets may be selected. In various implementations, this context or state may also include one or more soil sensing constraints. Soil sensing constraints may come in numerous forms depending on a variety of factors, such as the type of crops being grown, phenotypic traits of plants depicted in the acquired images (e.g., size, color, leaf/fruit/flower density, etc.), types of plants depicted in the acquired images (e.g., crops versus weeds), the type of soil analysis being performed (e.g., detecting prior application of fertilizer, detecting soil moisture, detecting organic content, etc.), and so forth.

As a few examples, soil sensing constraints may include: an optimal distance or range of distances between a soil sensing target and identified plant(s) (e.g., it may be preferable to take a soil sample within n inches of a crop or weed); a location on the ground of a prior fertilizer injection (e.g., recorded when those injections are implemented); a location between rows of plants; an optimal density at which soil sensing should be performed, and so forth. To account for the soil sensing constraints and the locations of identified plants near the vehicle, in some implementations, an objective function may be optimized with respect to the one or more soil sensing targets, subject to the one or more soil sensing constraints. This optimization may include, for instance, simulated annealing or linear programming.

Once the soil sensing targets are selected, soil sensing may be performed at those soil sensing targets. If lab-based soil analysis is being performed, then a soil sample may be extracted at one or more of the soil sensing targets. For example, a manipulator such as a robot arm may include an end effector that is configured to extract a soil sample from the ground and store it in a soil reservoir on the vehicle. These extracted soil samples may then be transported to a lab for analysis. If proximal soil analysis is being performed, then one or more of the aforementioned proximal soil sensors may be inserted an appropriate distance into the ground so that the proximal soil sensing may be implemented. In some implementations, the proximal soil sensor may be mounted on a robot arm, e.g., as an end effector. In other implementations, other types of manipulators may be used to extend proximal soil sensor(s) into soil sensing targets on the ground.

In some implementations, signals other than imagery acquired by vision sensor(s) may be incorporated into the context or state and thereby may be used to select soil sensing targets. For example, real time soil measurements obtained in the field using proximal soil sensors carried by the vehicle may be analyzed and used, alone or in combination with the imagery captured by the vision sensor(s), to select additional soil sensing targets and/or to alter existing soil sensing targets. For example, if a measurement obtained by a proximal soil moisture sensor reveals that the soil is dry at a particular location, that location may be avoided when another type of soil sensing that is reliant on moisture is being performed. Other signals that may be considered when selecting soil sensing targets may include, for instance, climate data, historical precipitation/irrigation data, past application of chemicals such as fertilizers or herbicides, historical crop rotation, observed and/or predicted growth trajectories, and so forth.

FIG. 1A illustrates an environment in which one or more selected aspects of the present disclosure may be implemented, in accordance with various implementations. The example environment includes a plurality of client devices $106_{1-X}$, a soil targeting system 102, and a plurality of vehicles $108_{1-M}$. Each of components $106_{1-X}$, 102, and 108 may communicate, for example, through a network 110. Soil targeting system 102 is an example of an information retrieval system in which the systems, components, and techniques described herein may be implemented and/or with which systems, components, and techniques described herein may interface.

An individual (which in the current context may also be referred to as a "user") may operate a client device 106 to interact with other components depicted in FIG. 1A. Each component depicted in FIG. 1A may be coupled with other components through one or more networks 110, such as a local area network ("LAN") or wide area network ("WAN") such as the Internet. Each client device 106 may be, for example, a desktop computing device, a laptop computing device, a tablet computing device, a mobile phone computing device, a computing device of a vehicle of the participant (e.g., an in-vehicle communications system, an in-vehicle entertainment system, an in-vehicle navigation system), a standalone interactive speaker (with or without a display), or a wearable apparatus that includes a computing device, such as a head-mounted display ("HMD") that provides an AR or VR immersive computing experience, a "smart" watch, and so forth. Additional and/or alternative client devices may be provided.

Each of client devices 106 and soil targeting system 102 may include one or more memories for storage of data and software applications, one or more processors for accessing data and executing applications, and other components that facilitate communication over a network. The operations performed by client device 106 and/or soil targeting system 102 may be distributed across multiple computer systems. In some implementations, soil targeting system 102 may be implemented as, for example, computer program(s) running on one or more computers in one or more locations that are coupled to each other through a network.

Each client device 106 may operate a variety of different applications that may be used, for instance, to coordinate soil analysis using techniques described herein. For example, a first client device $106_1$ operates agricultural task client 107 (e.g., which may be standalone or part of another application, such as part of a web browser). Another client device $106_X$ may take the form of a HMD that is configured to render 2D and/or 3D data to a wearer as part of a VR immersive computing experience. For example, the wearer of client device $106_X$ may be presented with 3D point clouds representing various aspects of objects of interest, such as fruits of crops, weeds, etc. The wearer may interact with the presented data, e.g., using HMD input techniques such as gaze directions, blinks, etc., to coordinate vehicles 108 using techniques described herein.

Figure 1B:
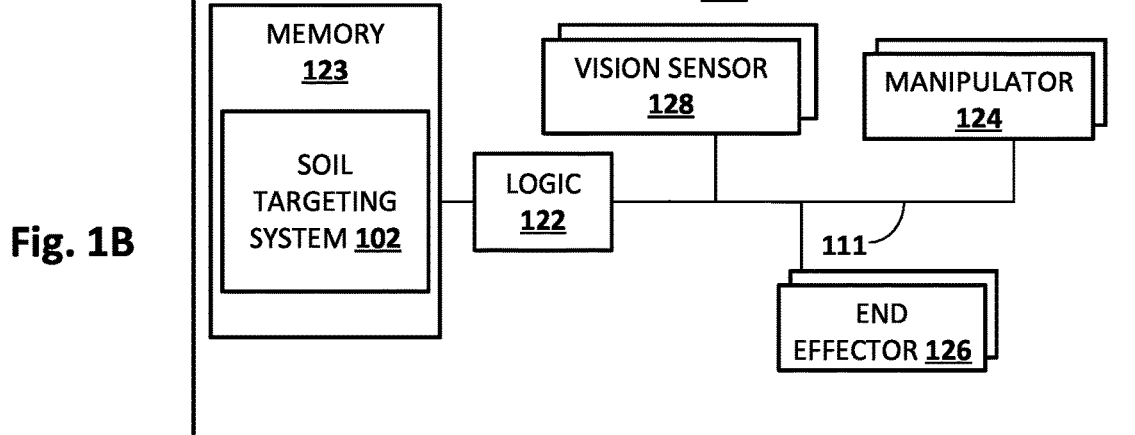
FIG. 1B schematically depicts an example vehicle configured with selected aspects of the present disclosure.

In various implementations, soil targeting system 102 may include a vision data analysis engine 112, a constraint engine 114, a targeting engine 116, and/or one or more databases 118 for storing various data used by and/or generated by components 112-116, such as sensor data gathered by sensors carried by vehicles $108_{1-M}$, information about available vehicles and/or proximal soil sensors, and so forth. In some implementations, one or more of engines 112-116 may be omitted. In some implementations, all or aspects of one or more of engines 112-116 may be combined. In some implementations, one or more of engines 112-116 may be implemented in a component that is separate from soil targeting system 102. In some implementations, one or more of engines 112-116, or any operative portion thereof, may be implemented by client device 106 and/or by logic carried by (e.g., integral with, contained in a modular device mounted to) a vehicle 108. For example, and as depicted in FIG. 1B, in some implementations, a vehicle 108 may implement all or a portion of soil targeting system 102 locally.

In this specification, the term "database" and "index" will be used broadly to refer to any collection of data. The data of the database and/or the index does not need to be structured in any particular way and it can be stored on storage devices in one or more geographic locations. Thus, for example, database(s) 118 may include multiple collections of data, each of which may be organized and accessed differently.

Individual vehicles $108_{1-M}$ may take various forms, such as a tractor $108_1$ with a boom sprayer 130 mounted to it, a robot (not depicted) that is propelled along a wire, track, rail or other similar component that passes over and/or between crops, a wheeled robot $108_2$, a robot $108_M$ that propels itself using one or more tracks, or any other form of vehicle capable of being propelled or propelling itself through agricultural areas. In some implementations, one or more modular computing devices (also referred to as "sensor packages") may be mounted to a vehicle and may be configured to perform selected aspects of the present disclosure, including aspects of operations described herein as being performed by soil targeting system 102. For example, in FIG. 1, multiple modular computing devices $109_{1-N}$ are mounted at selected location(s) to the boom sprayer 130 that is affixed to tractor $108_1$.

Vision data analysis engine 112 may be configured to receive or obtain, e.g., from one or more of vehicles $108_{1-M}$, 2D and/or 3D vision data. In some implementations, vision data analysis engine 112 may receive other robot sensor data as well. This other sensor data may include, for instance, position coordinates such as inertial measurement units ("IMUs"), real-time kinematic ("RTK") coordinates, GPS coordinates, temperature readings, humidity readings, etc. Based on analysis of vision data received from various vehicles 108 while scouting crops, vision data analysis engine 112 may perform various types of image processing analysis to detect plants and/or various phenotypic traits and/or conditions of plants. These phenotypic traits and/or conditions may include, but are not limited to, morphology (above ground and/or below ground), type (e.g., genus, species), maturity level (e.g., per se or relative to a crop cycle), plant health, size, shape, leaf density, flower density, fruit density, pod density, fruit size, and so forth.

The types of image processing that may be performed by vision data analysis engine 112 may vary among implementations. In some implementations, vision data analysis engine 112 may analyze 2D and/or 3D vision data to segment and/or classify individual plants within digital images, and/or detect phenotypic trait(s) of those plants. Vision data analysis engine 112 may utilize a variety of different techniques, including but not limited to appearance-based methods such as edge matching, divide-and-conquer, gradient matching, grayscale matching, histograms, and/or feature-based methods such as interpretation trees, pose clustering, geometric hashing, scale-invariant feature transform ("SIFT"), speeded up robust features ("SURF"), trained machine learning models (e.g., CNNs), and so forth.

Constraint engine 114 may be configured to perform selected aspects of the present disclosure to determine, select, and/or activate one or more soil sensing constraints that are imposed on the selection of soil sensing targets that is performed by targeting engine 116. In some implementations, constraint engine 114 may determine, select, and/or activate soil sensing constraints dynamically in the field, e.g., based on plants and/or plant attributes detected by vision in imagery acquired by vision sensor(s) carried by a vehicle. As mentioned previously, soil sensing constraints may include, but are not limited to, an optimal range of distances between a soil sensing target and one or more of the identified plants, a location on the ground of a prior chemical application, a location between rows of plants, and so forth.

Constraint engine 114 may determine, select, and/or activate various soil sensing constraints depending on a variety of signals and/or factors. A primary factor for determining, selecting, or activating soil sensing constraints is the soil properties being measured. Some soil properties and/or soil property values may be desirable or undesirable depending on the type of crop being grown, goals of the grower, historical or planned crop rotations, and so forth. Another factor that may be used by constraint engine 114 to determine, select, and/or activate soil sensing constraints may include historical application of chemicals such as fertilizers, pesticides, herbicides, etc. Indiscriminate spraying of chemicals across a field is increasingly being replaced with targeted injection of chemicals directly into the ground. Chemical injection has a variety of advantages over chemical spraying, such as decreasing waste, reducing unintentional application to untargeted areas, and so forth. These targeted injections may be performed as selected injection locations in the soil, such as some distance between rows, selected distances from plants, etc. These injection locations may be associated with and/or impose various soil sensing constraints.

Targeting engine 116 may be configured to perform selected aspects of the present disclosure to determine one or more locations of the one or more identified plants relative to the vehicle, and based on those location(s), select one or more soil sensing targets on the ground near the vehicle. In various implementations, targeting engine 116 selects these soil sensing targets subject to the soil sensing constraints determined, selected, and/or activated by constraint engine 114. For example, targeting engine 116 may be configured to optimize an objective function with respect to the one or more soil sensing targets, subject to the one or more soil sensing constraints. This optimization may be performed using various techniques. In some implementations, simulated annealing and/or linear programming may be employed, but these are not meant to be limiting.

FIG. 1B schematically depicts an example architecture of a vehicle 108, in accordance with various implementations. Vehicle 108 may take various forms, such as those described previously. In various implementations, vehicle 108 may include logic 122. Logic 122 may take various forms, such as a real time controller, one or more processors, one or more field-programmable gate arrays ("FPGA"), one or more application-specific integrated circuits ("ASIC"), and so forth. In some implementations, logic 122 may be operably coupled with memory 123. Memory 123 may take various forms, such as random access memory ("RAM"), dynamic RAM ("DRAM"), read-only memory ("ROM"), Magnetoresistive RAM ("MRAM"), resistive RAM ("RRAM"), NAND flash memory, and so forth. In some implementations, memory 123 may store instructions that are executable by logic 122 to implement all, or constituent parts of, soil targeting system 102. That way, vehicle 108 can perform techniques described herein while offline, or at least without necessarily being required to consult with soil targeting system 102.

In some implementations, logic 122 may be operably coupled with one or more manipulators 124, one or more end effectors 126, and/or one or more vision sensors 128, e.g., via one or more buses 111. As used herein, a "manipulator" 124 may broadly refer to a mechanism that is used to facilitate the physical interaction with soil that is necessary for soil sensing, whether that physical interaction action be collecting a sample that is then transported to a laboratory for analysis, or in situ proximal soil sensing. In various implementations, manipulator 124 may be operable to extend an end effector (e.g., a proximal soil sensor) downward from vehicle 108 towards the soil. In some implementations, manipulator 124 may take the form of a kinematic chain of elements connected by joints, e.g., a robot arm.

As used herein, "end effector" 126 may refer to a variety of tools that may be operated to accomplish various tasks. For example, one type of end effector 126 takes the form of a claw with two opposing "fingers" or "digits." Such a claw is one type of "gripper" known as an "impactive" gripper. Other types of grippers may include but are not limited to "ingressive" (e.g., physically penetrating an object using pins, needles, etc.), "astrictive" (e.g., using suction or friction or vacuum to pick up an object), or "contigutive" (e.g., using surface tension, freezing or adhesive to pick up object).

In the context of lab-based soil analysis, end effector 126 may be configured to extract a soil sample, and may include one or more of a shovel, scoop, rasp, blade(s), vacuum, etc. For example, in FIG. 1A, a manipulator 124 is mounted to boom sprayer 130 and can be operated to extend an end effector 126 in the form of a scoop into the soil. In the proximal soil sensing context, end effector 126 may include various types of proximal soil sensors. For example, robot $108_M$ includes a manipulator 124 in the form of a robot arm, with an end effector 126 in the form of a proximal soil sensor (e.g., to detect magnetism or electrical conductance of the soil).

Vision sensor(s) 128 may take various forms, including but not limited to 3D laser scanners or other 3D vision sensors (e.g., stereographic cameras used to perform stereo visual odometry) configured to provide depth measurements, 2D cameras, light sensors (e.g., passive infrared), and so forth. While not depicted in FIG. 1B, vehicle 108 may be equipped with other types of sensors as well, including but not limited to force sensors, pressure sensors, pressure wave sensors (e.g., microphones), proximity sensors (also referred to as "distance sensors"), depth sensors, torque sensors, barcode readers, radio frequency identification ("RFID") readers, radars, range finders, accelerometers, gyroscopes, compasses, position coordinate sensors (e.g., global positioning system, or "GPS"), speedometers, and so forth.

Figure 2:
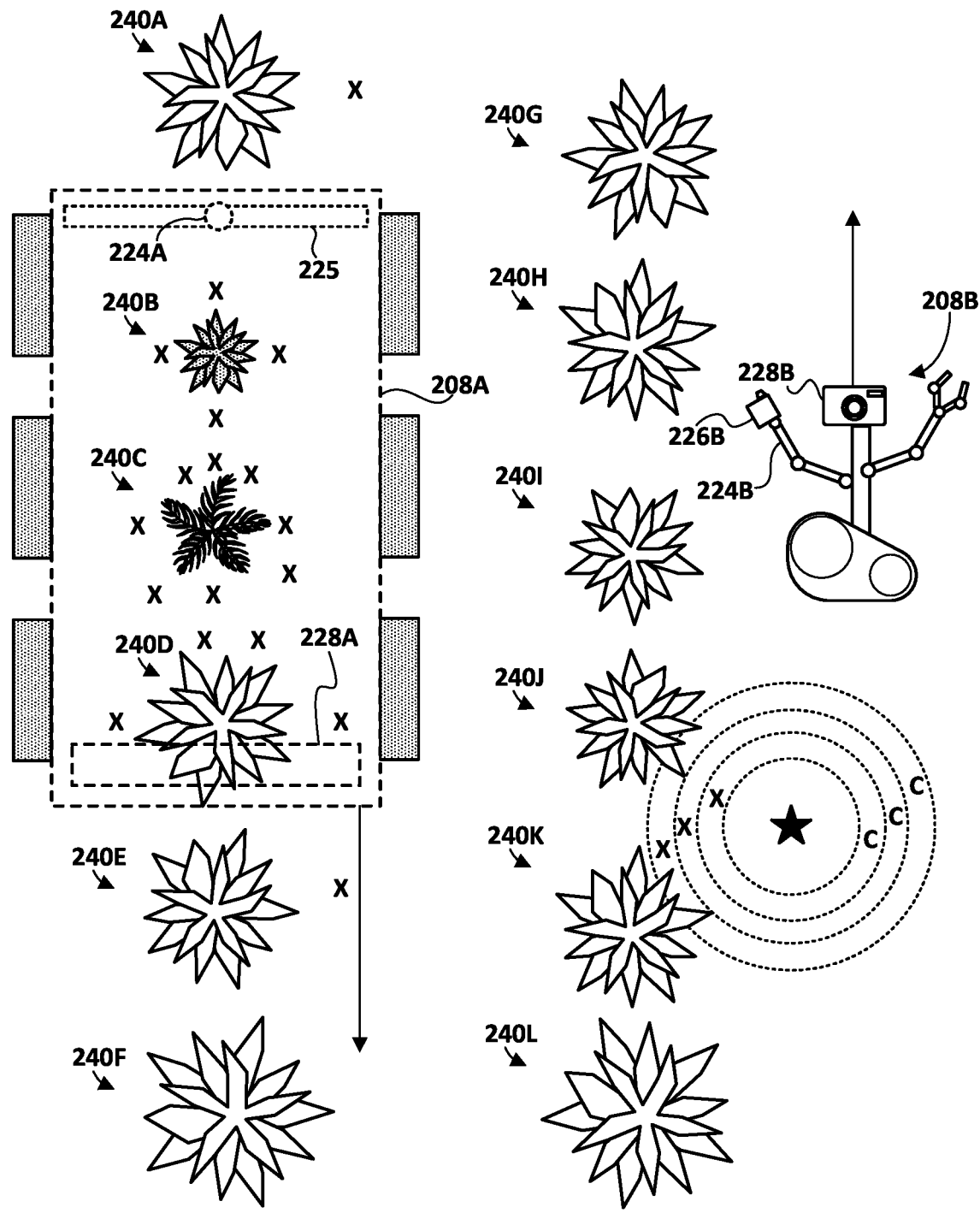
FIG. 2 depicts an example field of plants being acted upon by multiple vehicles configured with selected aspects of the present disclosure.

FIG. 2 depicts an example field of plants 240A-L being acted upon by multiple vehicles 208A-B. First vehicle 208A takes the form of a wheeled robot that straddles (i.e., so that its wheels flank) the first row of plants 240A-F. First vehicle 208A is moving in the downward direction and is both processing vision data it gathers about a first row of plants $240_{1-6}$ using its vision sensor 228A, as well as performing soil sensing. As noted previously, in various implementations, first vehicle 208A may have onboard all or parts of soil targeting system 102 so that it can make use of the vision data locally.

First vehicle 208A may also include a manipulator 224A—depicted with dashed lines because it is underneath first vehicle 208A—that is movable laterally along a track 225 (also depicted in dashed lines). Thus, between operating first vehicle 208A to move forward (down in FIG. 2) or backward and moving manipulator 224A laterally along track 225, it is possible to position manipulator 224A to virtually any position on the ground that first vehicle passes or is capable of passing over. Once in position, manipulator 224A can be operated to extend downward so that an end effector (not depicted in FIG. 2) can be operated to either extract a soil sample for laboratory analysis or perform proximal soil sensing. This type of laterally moving manipulator is just one example. In other implementations, first vehicle may be equipped with other types of manipulators, such as robot arms with greater freedom of movement, manipulators that can tilt at an angle relative to a normal extending from the ground, manipulators that extend from points on first vehicle other than its undercarriage, and so forth.

Second vehicle 208B, by contrast, is a track-propelled robot equipped with a manipulator 224B in the form of a robot arm, with an end effector 226B in the form of a proximal soil sensor. In addition, second vehicle 208B moves alongside, rather than over, second row of plants 240G-L. Otherwise, second vehicle 208B may operate on second row of plants 240G-L similarly to first vehicle 208A, e.g., using its own vision sensor 228B to gather data that is processed locally, so that second vehicle 208B can perform effective soil sensing.

In the first row of plants 240A-F, first vehicle 208A has selected and/or has already performed soil sensing at the locations on the ground marked with X's. The type of soil sensing performed at these soil sensing targets may vary depending on the goals of the grower, the type and/or state of the plant detected in the imagery captured by vision sensor 228A, and so forth. First plant 240A appears relatively healthy and is a type of plant that is expected to be found (i.e. the crop being grown). Accordingly, a single soil sensing target (X) was selected to one side, and may be a soil measurement of general interest, such as moisture, pH, organic content, etc. Alternatively, if the desired type of crop is spotted and appears healthy, no soil measurements may be performed.

As first vehicle 208A travels down the row of plants 240A-F and vision sensor 228A acquires image(s) of second plant 240B, onboard image processing confirms that second plant 240B is of the desired type. However, as indicated by the shading in FIG. 2, the state of second plant 240B appears to be unhealthy. This could be for a variety of reasons, such as poor quality soil, pest infestation, plant disease, improper irrigation, etc. To ascertain the extent to which soil quality contributed to the suboptimal health of second plant 240B, a plurality of soil sensing targets (four in FIG. 2) are selected at points surrounding second plant 240B. Selecting soil sensing targets at such increased numbers and/or density may better enable a determination of whether the soil quality is a contributing factor. Each of these soil sensing targets may be for the same type of soil analysis, or for different types of soil analysis (e.g., one for moisture, another for ph, another for organic content).

There may be multiple underlying soil issues that potentially contribute to a plant's condition. Each potential soil issue may be confirmed or eliminated using a different type of soil analysis. For example, a plant may have a rotting appearance due to one or more of excess moisture content in the soil, insufficient organic content, fungus present in the soil, etc. Accordingly, in some implementations, vision data analysis engine 112 may process images captured by vision sensors to generate a probability distribution over multiple different types of soil analysis that are available to investigate these potential causes. For example, a machine learning model such as a CNN or other type of model may be applied to image(s) to generate different probabilities of different types of available soil analysis (e.g., dictated by which proximal sensors are available on a vehicle) being effective at determining underlying soil issues. In some implementations, such a machine learning model may be trained using training images that are labeled or otherwise associated with "ground truth" soil measurements that effectively revealed soil-based causes of depicted plant(s)' conditions. To the extent the probability distribution diverges from the ground truth soil measurements, techniques such as back propagation and/or gradient descent may be used to train the model, e.g., by optimizing or minimizing an objective function.

Referring back to FIG. 2, in some implementations, the soil sensing targets around second plant 240B may be selected to be within some physical distance or range of distances from second plant 240B. In some such implementations, this distance or range of distances may be selected based at least in part on a context or state of second plant 240B. For example, if some sort of rot is detected, e.g., using a CNN trained to generate probabilities of various causes of rot, the soil sensing targets may be selected to be as close to the roots of second plant 240B as possible, e.g., to determine whether second plant 240B is receiving too much water, and/or whether there is a fungus present that is causing the rot.

As first vehicle 208A travels farther down the row of plants 240A-F, third plant 240C may be classified in imagery acquired by vision sensor 228A as being the wrong type of plant, such as a weed. In response, a number of soil sensing targets are selected at various positions around third plant 240C. In some implementations, these soil sensing targets may be selected based at least in part on the type of weed that is detected, e.g., using a CNN trained to classify weeds. Soil samples may be more or less informative at different distances from different types of weeds, for instance.

In some implementations, the number and/or density of soil sensing targets may increase as more plants with suboptimal health and/or of undesired types are detected, especially if they are detected consecutively. In FIG. 2, for instance, third plant 240B is determined to have problems (weed) immediately after second plant 240B is determined to have suboptimal health. Because these plants are adjacent to each other, there is a distinct possibility that the soil they share has properties that are not conducive to successful growth. Accordingly, first vehicle 208A (or more particularly, the instance of soil targeting system 102 it executes locally) may transition to a state of heighted soil scrutiny where soil sensing targets are selected in increased numbers and/or at increased densities, as shown in the area surrounding third plant 240C.

This heighted soil scrutiny may be maintained until various events occur. For example, the next plant, fourth plant 240D, is the desired type of crop and appears healthy. Consequently, while greater numbers of soil sensing targets are selected between third plant 240C and fourth plant 240D, past (or below in FIG. 2) fourth plant 240D, the number and/or density of soil sensing targets is decreased. By the time another healthy crop, fifth plant 240E, is detected, first vehicle 208A has reverted back to selecting a single soil sensing target adjacent fifth plant 240E.

In some implementations, in addition to or instead of detected plants/plant traits/plant classifications, selection of soil sensing targets may turn on knowledge of prior injection of chemicals such as fertilizer or herbicide into the soil. Turning to second vehicle 208B and second row of plants 240G-L, between plants 240J and 240K, a star represents a location at which fertilizer was previously injected into the soil. The concentric rings drawn around this injection location represent various distances from the location.

As indicated by the X's, second vehicle 208B performed proximal soil sensing (using end effector 226B in the form of a proximal soil sensor) at multiple different distances from the injection location. Selecting soil sensing targets in such a pattern may provide information about a gradient of the fertilizer spread through the soil. For example, fertilizer may pass more slowly or to a lesser extent through dense soil (e.g., with considerable clay content) than it would through more permeable soil. The soil sensing targets indicated by the X's may allow for measurement of such a gradient of spread.

In some implementations, second vehicle 208B may also select "control" soil sensing targets, as indicated by the C's in FIG. 2. These control sensing targets may be taken at locations that are devoid of plants. One possible reason for doing so is that fertilizer may be absorbed by roots of plants, which may cause the soil near those plants to have lower levels of fertilizer. By selecting additional control soil sensing targets where no such plant absorption would occur, it is possible to compare the measures taken at the X's to the measurements taken at the C's to determine how much fertilizer was absorbed by nearby plants 240J and 240K.

Figure 3:
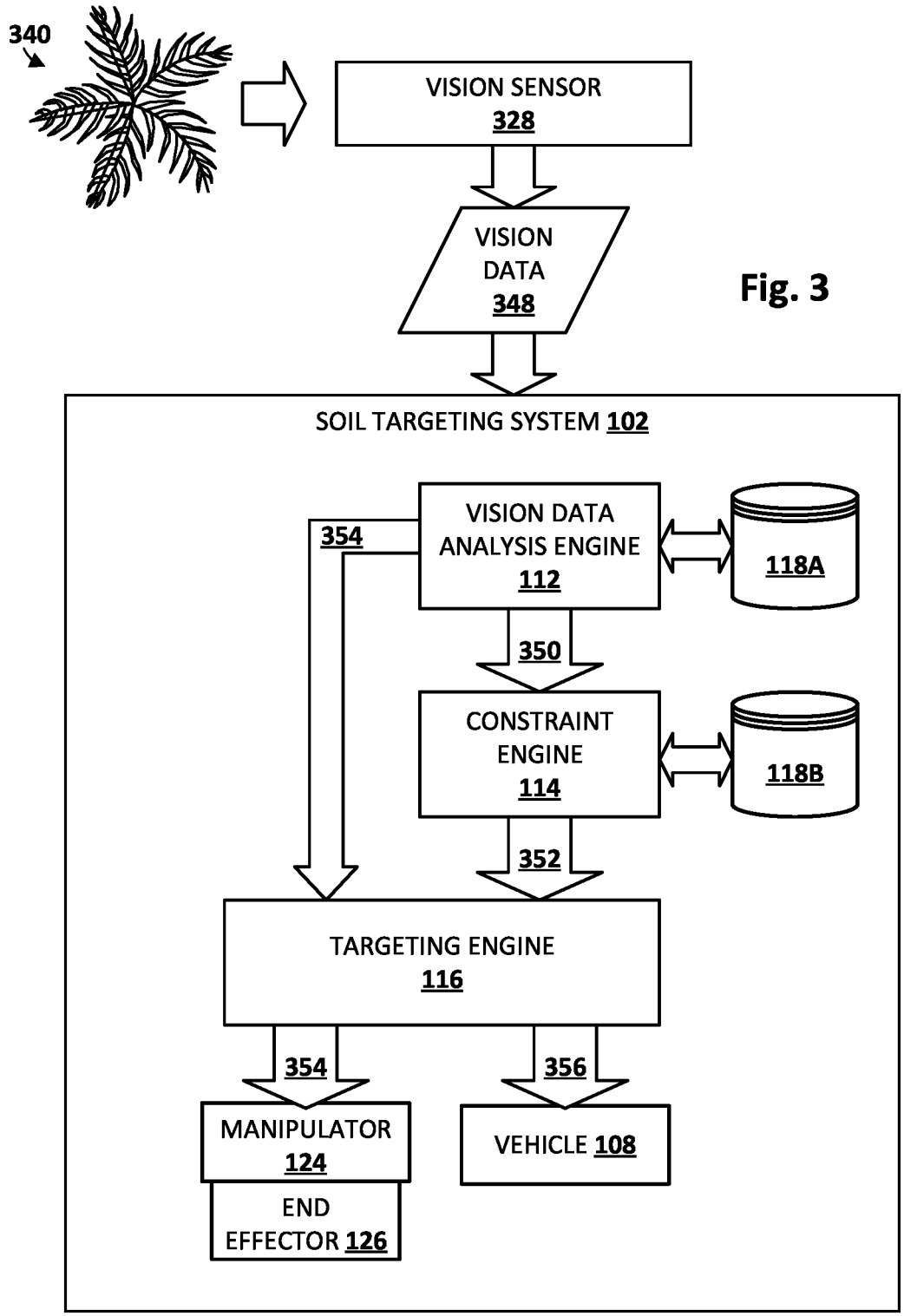
FIG. 3 schematically depicts one example of how vision data may be processed and used to select soil sensing targets, in accordance with various implementations.

FIG. 3 schematically depicts an example of how various components described herein may process data in order to select optimal soil sensing targets. Starting at top left, a plant 340 may be sensed by vision sensor 328 (e.g., carried by a vehicle) to generate vision data 348. This vision data 348 may be processed by vision data analysis engine 112, e.g., using one or more routines or machine learning models stored in a first database 118A. For example, one or more CNNs may be used to process vision data 348 to segment and/or annotate detected plants with various information, such as traits, health, etc.

The annotated vision data 350 may be provided to constraint engine 114. Constraint engine 114 may determine and/or select (e.g., from a database 118B) one or more soil sensing constraints based on the annotation(s). For example, plants that are detected to be afflicted with a soil-quality-based malady may trigger a particular type of soil analysis. That type of soil analysis may have its own constraints, such as samples need to be taken at some predetermined distance (or within a range of distances) from the plant detected having the malady. The constraint(s) 352 selected and/or determined by constraint engine 114 may be provided to targeting engine 116.

Meanwhile, the annotated images and/or any other inferences drawn by vision data analysis engine 112 may also be provided to targeting engine 116. Targeting engine 116 may be first configured to determine one or more locations of the one or more identified plants relative to the vehicle. Put another way, targeting engine 116 may localize the detected plants. Targeting engine 116 may localize plants detected by vision data analysis engine 112 in vision data 348 based on a variety of different signals. In some implementations, vision sensor 328 or a separate depth sensor may obtain depth or range measurements, which may be used by targeting engine 116 to estimate distances from vision sensor 328 to various targets, such as detected plants, soil sensing targets, and the like. The vehicle's position, trajectory, and/or velocity may also be considered by targeting engine 116. For example, a distance traveled by the vehicle since an image analyzed by vision data analysis engine 112 was captured may be taken into account when determining a location of a plant detected in that image, relative to the vehicle.

Additionally or alternatively, the location(s) of the identified plant(s) relative to the vehicle may be determined by targeting engine 116 based at least in part on extrinsic parameters of vision sensor 328 relative to the vehicle. For example, the translational location and/or orientation of vision sensor 328 relative to a world frame and/or the vehicle may be used by targeting engine 116 in conjunction with a range between vision sensor 328 and a detected plant to determine the detected plant's location relative to vehicle.

Targeting engine 116 also may take into account an angle between vision sensor 328 and the detected plant to determine the plant's location relative to the vehicle. Intrinsic parameters of vision 328, such as zoom, may also be considered.

After the plants detected by vision data analysis engine 112 in vision data 348 are localized relative to the vehicle, those locations, along with the constraints provided by constraint engine 114 and other data (e.g., classifications, phenotypic traits) generated by vision data analysis engine 112, may collectively form the context or state of the vehicle. Based on this context or state, targeting engine 116 may select soil sensing targets on the ground (e.g., in the soil). As noted previously, in some implementations, targeting engine 116 may optimize an objective function with respect to the one or more soil sensing targets, subject to the one or more soil sensing constraints, using techniques such as simulated annealing and/or linear programming to name a few.

Once targeting engine 116 has determined and/or selected the soil sensing targets on the ground, it may provide commands 354 to manipulator 124 and/or end effector 126 to perform soil sensing at these soil sensing targets. Additionally or alternatively, in some implementations, targeting engine 116 may provide a map or list of the soil sensing targets to another component, such as a robot controller or controller associated with manipulator 124, and this controller may use those soil sensing targets to perform soil sensing. In some implementations, targeting engine 116 may provide commands and/or soil sensing targets to vehicle 108, e.g., so that vehicle can move (or be moved by an operator in response to audible or visual prompts) forward or backward to effectuate soil sensing.

Figure 4:
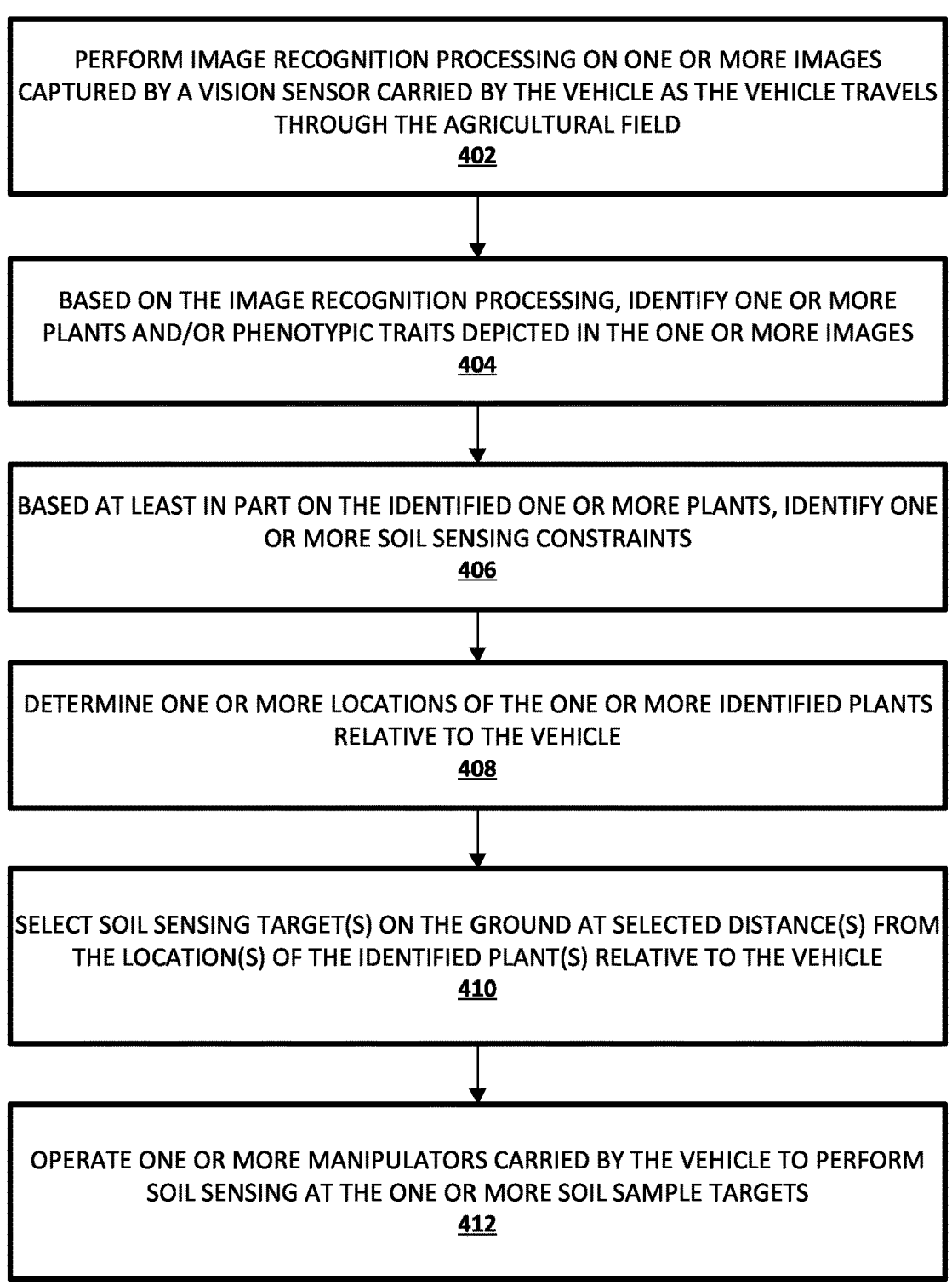
FIG. 4 a flowchart of an example method in accordance with various implementations described herein.

FIG. 4 illustrates a flowchart of an example method 400 for practicing selected aspects of the present disclosure. The operations of FIG. 4 can be performed by one or more processors, such as one or more processors of the various computing devices/systems described herein, such as by soil targeting system 102. For convenience, operations of method 400 will be described as being performed by a system configured with selected aspects of the present disclosure. Other implementations may include additional steps than those illustrated in FIG. 4, may perform step(s) of FIG. 4 in a different order and/or in parallel, and/or may omit one or more of the steps of FIG. 4.

At block 402, the system, e.g., by way of vision data analysis engine 112, may perform object recognition processing on one or more images captured by a vision sensor (e.g., 128, 228A-B, 328) carried by the vehicle (e.g., 108, 208) as the vehicle travels through an agricultural field. As noted previously, this object recognition processing may employ a variety of techniques to detect plants and other objects that influence soil sensing target selection. These techniques may include, for instance, CNNs trained for plant or phenotypic trait classification, or any of the other techniques mentioned previously.

Based on the object recognition processing of block 402, at block 404, the system, e.g., by way of vision data analysis engine 112, may identify one or more plants and/or phenotypic traits depicted in the one or more images. For example, the image(s) may be segmented or otherwise annotated (e.g., with bounding boxes) to distinguish plants from bare soil, as well as indicate the types of those plants and/or traits of those plants.

Based at least in part on the one or more plants identified at block 404, at block 406, the system, e.g., by way of constraint engine 114, may identify one or more soil sensing constraints. For example, if a plant is classified as unhealthy due to over- or under-application of some other chemical, constraint engine 114 may determine that soil sensing that is directed to detecting that chemical is warranted. And that particular type of soil sensing may have various inherent constraints, such as optimal distance(s) from plants at which to take measurements. Or, there may be multiple potential causes for the plant's poor health. More generally, in various implementations, constraint engine 114 may determine and/or select soil sensing constraints based on the previously-mentioned context or state. This context or state may further include, for instance, environmental data, climate data, stewardship data, and so forth.

At block 408, the system, e.g., by way of targeting engine 116, may determine one or more locations of the one or more identified plants relative to the vehicle. As noted previously, these location(s) may be determined by targeting engine 116 based on a variety of data points, such as extrinsics and intrinsics of the vision sensor, depth/range measurements, the vehicle's position and/or velocity (currently and/or relative to acquisition of the examined image), and so forth.

Based on the one or more locations of the identified plant(s) relative to the vehicle, as well as subject to the constraint(s) determined by constraint engine 114 at block 406, at block 410, the system, e.g., by way of targeting engine 116, may select one or more soil sensing targets on the ground at one or more selected distances from the one or more locations of the one or more identified plants relative to the vehicle. At block 412, the system may operate one or more manipulators (e.g., 124, 224A-B) carried by the vehicle to perform soil sensing at the one or more soil sensing targets.

Figure 5:
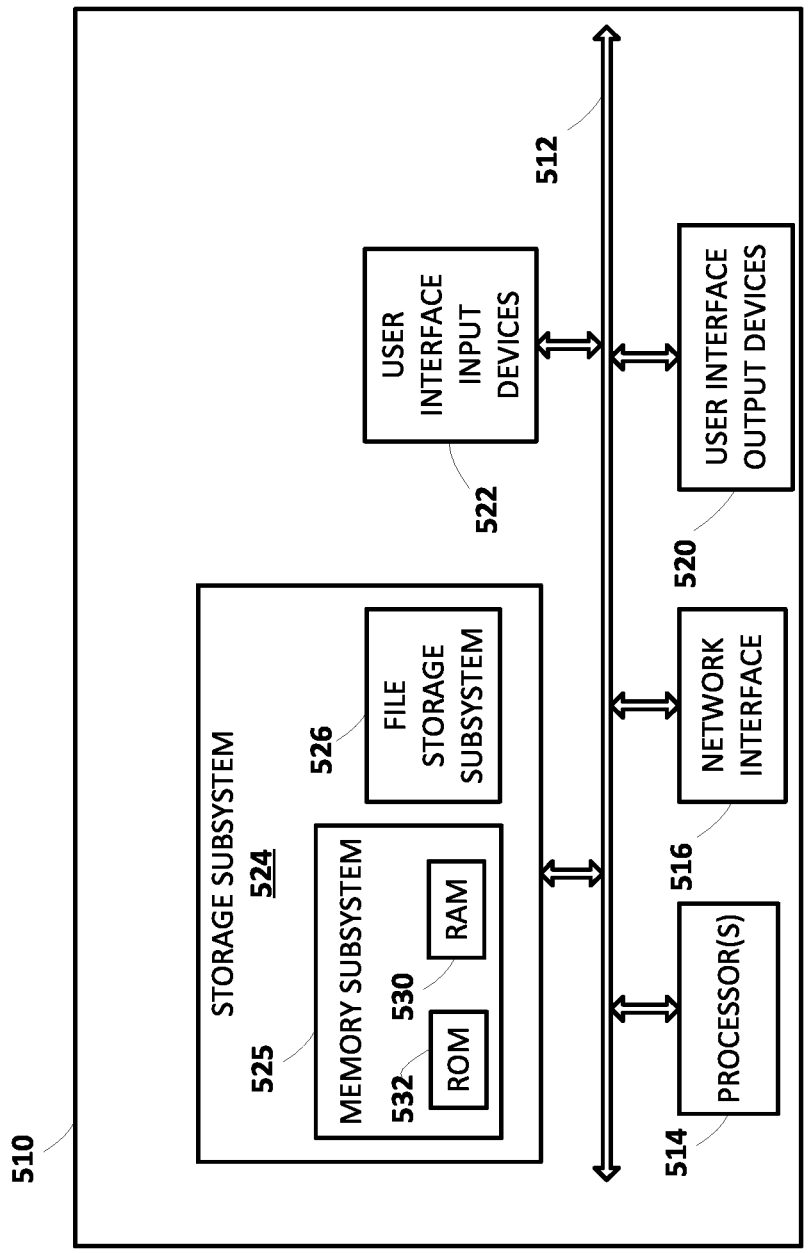
FIG. 5 schematically depicts an example architecture of a computer system.

FIG. 5 is a block diagram of an example computing device 510 that may optionally be utilized to perform one or more aspects of techniques described herein. Computing device 510 typically includes at least one processor 514 which communicates with a number of peripheral devices via bus subsystem 512. These peripheral devices may include a storage subsystem 524, including, for example, a memory subsystem 525 and a file storage subsystem 526, user interface output devices 520, user interface input devices 522, and a network interface subsystem 516. The input and output devices allow user interaction with computing device 510. Network interface subsystem 516 provides an interface to outside networks and is coupled to corresponding interface devices in other computing devices.

User interface input devices 522 may include a keyboard, pointing devices such as a mouse, trackball, touchpad, or graphics tablet, a scanner, a touch screen incorporated into the display, audio input devices such as voice recognition systems, microphones, and/or other types of input devices. In some implementations in which computing device 510 takes the form of a HMD or smart glasses, a pose of a user's eyes may be tracked for use, e.g., alone or in combination with other stimuli (e.g., blinking, pressing a button, etc.), as user input. In general, use of the term "input device" is intended to include all possible types of devices and ways to input information into computing device 510 or onto a communication network.

User interface output devices 520 may include a display subsystem, a printer, a fax machine, or non-visual displays such as audio output devices. The display subsystem may include a cathode ray tube (CRT), a flat-panel device such as a liquid crystal display (LCD), a projection device, one or more displays forming part of a HMD, or some other mechanism for creating a visible image. The display subsystem may also provide non-visual display such as via audio output devices. In general, use of the term "output device" is intended to include all possible types of devices and ways to output information from computing device 510 to the user or to another machine or computing device.

Storage subsystem 524 stores programming and data constructs that provide the functionality of some or all of the modules described herein. For example, the storage subsystem 524 may include the logic to perform selected aspects of the method 400 described herein, as well as to implement various components depicted in FIG. 1.

These software modules are generally executed by processor 514 alone or in combination with other processors. Memory 525 used in the storage subsystem 524 can include a number of memories including a main random access memory (RAM) 530 for storage of instructions and data during program execution and a read only memory (ROM) 532 in which fixed instructions are stored. A file storage subsystem 526 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 526 in the storage subsystem 524, or in other machines accessible by the processor(s) 514.

Bus subsystem 512 provides a mechanism for letting the various components and subsystems of computing device 510 communicate with each other as intended. Although bus subsystem 512 is shown schematically as a single bus, alternative implementations of the bus subsystem may use multiple buses.

Computing device 510 can be of varying types including a workstation, server, computing cluster, blade server, server farm, or any other data processing system or computing device. Due to the ever-changing nature of computers and networks, the description of computing device 510 depicted in FIG. 5 is intended only as a specific example for purposes of illustrating some implementations. Many other configurations of computing device 510 are possible having more or fewer components than the computing device depicted in FIG. 5.

While several implementations have been described and illustrated herein, a variety of other means and/or structures for performing the function and/or obtaining the results and/or one or more of the advantages described herein may be utilized, and each of such variations and/or modifications is deemed to be within the scope of the implementations described herein. More generally, all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific implementations described herein. It is, therefore, to be understood that the foregoing implementations are presented by way of example only and that, within the scope of the appended claims and equivalents thereto, implementations may be practiced otherwise than as specifically described and claimed. Implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

What is claimed is:

1. A method implemented by one or more processors while a vehicle travels through an agricultural field, the method comprising:
performing object recognition processing on one or more images captured by a vision sensor carried by the vehicle as the vehicle travels through the agricultural field;
based on the object recognition processing, identifying one or more plants depicted in the one or more images;
determining one or more locations of the one or more identified plants relative to the vehicle;
selecting one or more soil sensing targets on a ground of the agricultural field at one or more selected distances from the one or more locations of the one or more identified plants relative to the vehicle, wherein each of the one or more soil sensing targets corresponds to a position in the field to sense the one or more sensing targets; and
responsive to the vehicle being positioned near a location of an identified plant, operating one or more manipulators carried by the vehicle to perform soil sensing of a soil sensing target by positioning the one or more manipulators of the vehicle at the position corresponding to the soil sensing target.

2. The method of claim 1, wherein the one or more locations of the one or more identified plants relative to the vehicle are determined based at least in part on extrinsic parameters of the vision sensor relative to the vehicle.

3. The method of claim 1, wherein the one or more locations of the one or more identified plants relative to the vehicle are determined based at least in part on depth measurements obtained by the vision sensor or by another sensor carried by the vehicle.

4. The method of claim 1, wherein the selecting is further based on one or more soil sensing constraints.

5. The method of claim 4, wherein the one or more soil sensing constraints include an optimal range of distances between a soil sensing target and one or more of the identified plants.

6. The method of claim 4, wherein the one or more soil sensing constraints include a location on the ground of a prior fertilizer injection.

7. The method of claim 4, wherein the one or more soil sensing constraints include a location between rows of plants.

8. The method of claim 4, wherein the selecting comprises optimizing an objective function with respect to the one or more soil sensing targets, subject to the one or more soil sensing constraints.

9. The method of claim 8, wherein the optimizing comprises simulated annealing or linear programming.

10. The method of claim 1, wherein one or more of the manipulators comprises a robot arm.

11. The method of claim 10, wherein the robot arm includes an end effector configured to extract a soil sample for subsequent lab analysis.

12. The method of claim 10, wherein the robot arm includes, as an end effector, a proximal soil sensor.

13. A system comprising one or more processors and memory storing computer program instructions that, in response to execution of the computer program instructions by the one or more processors and while a vehicle comprising the one or more processors and computer program instructions travels through an agricultural field, cause the one or more processors to:
perform object recognition processing on one or more images captured by a vision sensor carried by the vehicle as the vehicle travels through the agricultural field;
based on the object recognition processing, identify one or more plants depicted in the one or more images;
determine one or more locations of the one or more identified plants relative to the vehicle;
select one or more soil sensing targets on a ground of the agricultural field at one or more selected distances from the one or more locations of the one or more identified plants relative to the vehicle, wherein each of the one or more soil sensing targets corresponds to a position in the field to sense the one or more sensing targets; and
responsive to the vehicle being positioned near a location of an identified plant, operate one or more manipulators carried by the vehicle to perform soil sensing of a soil sensing target by positioning the one or more manipulators of the vehicle at the position corresponding to the soil sensing target.

14. The system of claim 13, wherein the one or more locations of the one or more identified plants relative to the vehicle are determined based at least in part on extrinsic parameters of the vision sensor relative to the vehicle.

15. The system of claim 13, wherein the one or more locations of the one or more identified plants relative to the vehicle are determined based at least in part on depth measurements obtained by the vision sensor or by another sensor carried by the vehicle.

16. The system of claim 13, wherein the soil sensing targets are selected further based on one or more soil sensing constraints.

17. The system of claim 16, wherein the one or more soil sensing constraints include an optimal range of distances between a soil sensing target and one or more of the identified plants.

18. The system of claim 16, wherein the one or more soil sensing constraints include a location on the ground of a prior fertilizer injection.

19. The system of claim 16, wherein the one or more soil sensing constraints include a location between rows of plants.

20. A non-transitory computer-readable medium comprising computer program instructions that, in response to execution of the computer program instructions by one or more processors and while a vehicle comprising the one or more processors and computer program instructions travels through an agricultural field, cause the processor to:
perform object recognition processing on one or more images captured by a vision sensor carried by the vehicle as the vehicle travels through the agricultural field;
based on the object recognition processing, identify one or more plants depicted in the one or more images;
determine one or more locations of the one or more identified plants relative to the vehicle;
select one or more soil sensing targets on a ground of the agricultural field at one or more selected distances from the one or more locations of the one or more identified plants relative to the vehicle, wherein each of the one or more soil sensing targets corresponds to a position in the field to sense the one or more sensing targets; and
responsive to the vehicle being positioned near a location of an identified plant, operate one or more manipulators carried by the vehicle to perform soil sensing of a soil sensing target by positioning the one or more manipulators of the vehicle at the position corresponding to the soil sensing target.

\* \* \* \* \*